United States Patent [19]
Ostlund, Jr.

[11] Patent Number: 5,932,562
[45] Date of Patent: Aug. 3, 1999

[54] SITOSTANOL FORMULATION TO REDUCE CHOLESTEROL ABSORPTION AND METHOD FOR PREPARING AND USE OF SAME

[75] Inventor: Richard E. Ostlund, Jr., St. Louis, Mo.

[73] Assignee: Washington University, St. Louis, Mo.

[21] Appl. No.: 09/084,561

[22] Filed: May 26, 1998

[51] Int. Cl.$^6$ .......................... A61K 31/685; A61K 31/56

[52] U.S. Cl. .............................. 514/78; 514/182; 514/824

[58] Field of Search ................................ 514/78, 182, 824

[56] References Cited

U.S. PATENT DOCUMENTS 5,244,887  9/1993  Straub ...................................... 514/182

*Primary Examiner*—Kimberly Jordan
*Attorney, Agent, or Firm*—Zarley, McKee, Thomte, Voorhees & Sease

[57] ABSTRACT

Compositions useful to reduce cholesterol absorption. The compositions may be dosed in capsule or tablet form, or by adding either in liquid or dry powder form to foods and beverages. The compositions are an aqueous based homogeneous micellar mix which is dried to provide a mixture of finely-divided plant sterol, preferably sitostanol and lecithin. The mole ratio of the plant sterol, preferably sitostanol to lecithin, should be within the range of 1:1 to 1:10, preferably at least 1:2.

12 Claims, No Drawings

SITOSTANOL FORMULATION TO REDUCE CHOLESTEROL ABSORPTION AND METHOD FOR PREPARING AND USE OF SAME

GRANT REFERENCE

This application was in part supported from funding of the National Institutes of Health through research grant

FIELD OF THE INVENTION

This invention relates to a composition and method for reducing cholesterol absorption and serum cholesterol in humans.

BACKGROUND OF THE INVENTION

Phytosterols are plant sterols structurally similar to cholesterol that have been known for many years to reduce cholesterol absorption and serum cholesterol levels while not being absorbed themselves. Lowering of circulating cholesterol and low density lipoprotein cholesterol is an important part of a strategy to prevent and treat cardiovascular disease and especially coronary heart disease. Cholesterol absorption is a critical component of whole body cholesterol metabolism. Cholesterol derived from the diet and also from endogenous biliary secretion enters the intestine, and approximately 50% of the mixed intestinal load is absorbed, Bosner, M. S., Ostlund, R. E., Jr., Osofisan, O., Grosklos, J., Fritschle, C., Lange, L. G. 1993. The failure to absorb cholesterol quantitatively is therefore a key mechanism for the elimination of cholesterol from the body.

Drugs commonly used to treat high cholesterol levels have little or no effect on cholesterol absorption. For example, the potent new hydroxymethylglutaryl coenzyme A reductase inhibitors have a primary action to reduce cholesterol synthesis rather than increase cholesterol elimination. Bile acid sequestrants such as the ion-exchange resin cholestyramine act within the intestine but do not bind cholesterol and may actually increase cholesterol absorption when given chronically. McNamara, D. J., N. O. Davidson, P. Samuel, and E. H. Ahrens, Jr. 1980, Cholesterol absorption in man:effect of administration of clofibrate and/or cholestyramine. J. Lipid Res. 21:1058–1064. Although orally-administered neomycin reduces cholesterol absorption effectively, it is toxic and has the disadvantage of requiring chronic administration of a potent antibiotic, Samuel, P. 1979. Treatment of hypercholesterolemia with neomycin—A time for reappraisal. N. Engl. J. Med. 301:595–597. The drug Cytellin®, an aqueous suspension of mixed phytosterols, was produced by Eli Lilly Co. for treatment of elevated cholesterol, but it has not been sold since 1985. As seen, it is apparent that new inhibitors of cholesterol absorption would complement currently-available treatment for high serum cholesterol.

Since phytosterols are natural products which are non-toxic and inexpensive byproducts of food processing, they may be important in the treatment of individuals with mildly-increased serum cholesterol, or for the general population in food products or dietary supplements. The use of phytosterols could reduce the need for systemically-absorbed drugs.

Despite their potential attractiveness, the usefulness of phytosterols has been limited by small and erratic effectiveness and a large dosage requirement. For example, doses of 5–18 g sitosterol/day reduced serum cholesterol by 16–20%. Farquhar, J. W. and M. Sokolow, 1958. A dose-response study showed that 3–9 g/day of powdered sitosterol was needed to decrease serum cholesterol levels by 12%. Lees, A. M., H. Y. I. Mok, R. S. Lees, M. A. McCluskey, and S. M. Grundy.1977.Plant sterols as cholesterol-lowering agents:clinical trials in patients with hypercholesterolemia and studies of sterol balance, Atherosclerosis 28:325–338. To reduce the amount needed, recent experiments have used sitostanol instead of sitosterol because it appears to be more potent than other phytosterols and is non-absorbable, Sugano, J., H. Morioka, and I. Ikeda.(1977) A comparison of hypocholesterolemic activity of β-sitosterol and β-sitostanol in rats. J. Nutr.107:2011–2019. In subjects with severe hypercholesterolemia sitostanol at 1.5 g/day reduced serum cholesterol by 15%, Heinemann, T.,O. Leiss, and K. von Bergmann (1986) Effect of low-dose sitostanol on serum cholesterol in patients with hypercholesterolemia. Atherosclerosis 61:219–223. However, sitostanol at 3 g/day had no effect in subjects with moderate hypercholesterolemia. Denke, M. A. (1995), Lack of efficacy of low-dose sitostanol therapy as an adjunct to a cholesterol-lowering diet in men with moderate hypercholesterolemia. Am. J. Clin. Nutr. 61:392–396.

Several investigators have proposed ways to increase the solubility or bioavailability of phytosterols in order to make them more useful. Based on studies in rats and the finding that phytosterol esters are much more soluble in oil than the free sterols, it has been proposed to use phytosterol esters in oil to lower cholesterol absorption, Mattson, F. H., R. A. Volpenhein, and B. A. Erickson (1977), Effect of plant sterol esters on the absorption of dietary cholesterol. J. Nutr. 107:1139–1146. U.S. Pat. No. 5,502,045 describes the use of sitostanol ester in oil for the treatment of hypercholesterolemia in humans. It was found that 2.8 g sitostanol/day given as sitostanol ester in margarine reduced LDL cholesterol by 16%. Miettinen, T. A., P. Puska, H. Gylling, H. Vanhanen, and E. Vartiainen (1995), Reduction of serum cholesterol with sitostanol-ester margarine in a mildly hypercholesterolemic population. N. England J. Med. 333:1308–1312. However, the use of sitostanol ester dissolved in dietary fat has the disadvantage of requiring the administration of 23–50 g/day of dietary fat and of being 21% less effective at reducing cholesterol absorption in humans compared to the unesterified sterol. Mattson, F. H., S. M. Grundy, and J. R. Crouse, (1982), optimizing the effect of plant sterols on cholesterol absorption in man. Am. J. Clin. Nutr. 35:697–700.

Additional workers have investigated ways to improve the usefulness of unesterified phytosterols. In International patent Publication WO 95/00158 a complex of sitosterol and the unabsorbable dietary fiber pectin reduced serum cholesterol by 16.4% when given to hypercholesterolemic humans in a dose of 2.1 g/day. However, no measurements of an effect on cholesterol absorption were made, and the complex was only about 50% soluble even at strongly alkaline pH, suggesting that the bioavailability of the sitosterol component was limited.

U.S. Pat. 5,244,887 describes the use of stanols including sitostanol in food additives to reduce cholesterol absorption. In U.S. Pat. 5,244,887, for preparation of the additives, sitostanol is dissolved with an edible solubilizing agent such as triglyceride, an antioxidant such as tocopherol, and a dispersant such as lecithin, polysorbate 80, or sodium lauryl sulfate. However, no data were given to guide one in the selection of the most effective components and their amounts or specific methods of preparation. Effectiveness in reducing cholesterol absorption was also not determined. The preferred embodiment consisted of 25% by weight stanols in vegetable oil, but the solubility of sterols in oil is only 2%.

U.S. Pat. 5,118,671 describes the production of sitosterol-lecithin complexes for pharmaceutical use but does not consider oral use for cholesterol lowering.

Cholesterol is absorbed from an intestinal micellar phase containing bile salts and phospholipids which is in equilibrium with an oil phase inside the intestine. Delivery of phytosterol as a solid powder or aqueous suspension is not preferred because of the limited rate and extent of solubility in intestinal liquid phases. Esterification of the phytosterol with delivery through the oil phase of foods is an alternative route but has the disadvantage of use of edible oils as the carrier.

Accordingly, it is an object of the present invention to provide a delivery system for plant sterols, particularly sitostanol, which avoids an oil phase and which provides bioavailable sitostanol at a level which reduces cholesterol absorption, often as much as 37% or more.

Another objective of the present invention is to provide a water soluble composition which provides the sitostanol, not dissolved in fat, but rather combined with a phospholipid in an aqueous vesicular complex which can enter directly into the intestinal micellar phase and is therefore highly bioavailable.

Another objective of the present invention is to provide a composition of preferred enhanced solubility that contains a plant sterol, preferable sitostanol mixed with a mixture of phospholipids, namely lecithin and lysolecithin, which has water solubility in excess of 90%.

Another objective of the present invention is to provide a method for reducing cholesterol absorption from food products containing cholesterol by mixing finely divided water soluble powder of an aqueous homogeneous micellar mix of sitostanol and lecithin with a food product which is to be ingested.

A yet further objective of the present invention is to provide a method of manufacturing a dry, finely divided water soluble powder which contains a plant sterol, preferably sitostanol, and lecithin, which is highly water soluble, so that when in contact with an aqueous system it will provide an aqueous vesicular complex which can enter directly into the intestinal micellar phase to inhibit cholesterol absorption.

The method and manner of achieving each of the above objectives, as well as others, will become apparent from the detailed description of the invention which follows hereinafter.

SUMMARY OF THE INVENTION

A composition for inhibiting cholesterol absorption from the intestine is described. The composition comprises phytosterols, preferably sitostanol, dispersed in an aqueous base phospholipid, preferably lecithin. The mole ratio of sterol to lecithin should be 1:1 to 1:10, preferably 1:2 to 1:4.

The phytosterol-phospholipid complex is prepared by high shear mixing, for example by vortexing, mixing, sonicating or passing through a small orifice of a phytosterol: phospholipid mixture in water. The dispersed material is then either used as is or dried, for example, by lyophilization or spray-drying. The complex can be used in liquid form prior to any drying, or it can be dried as indicated, and then on contact with liquid it again forms an aqueous vesicular complex which can enter directly into the intestinal micellar phase. No fat is used as a carrier, and surprisingly the system, even when dried, does not change its physical structure from the micelles that contain vesicles, the majority of which contain some plant sterol and some lecithin.

DETAILED DESCRIPTION OF THE INVENTION

As previously mentioned, the current invention differs from prior art uses of plant sterols and sitostanol in many significant ways.

First, the dose needed to reduce cholesterol absorption is lower than previously reported, namely 25–300 mg of sitostanol. Second, the preferred formulation does not contain triglycerides or oils. The phytosterol is not dissolved in fat, but rather is combined with phospholipid to form an aqueous vesicular complex which can enter directly into the intestinal micelle phase. Third, the mix can be prepared in solid form by drying an aqueous sitostanol/lecithin vesicular formulation with retention of solubility in artificial bile. Fourth, the mix is effective when consumed separately from cholesterol-containing foods. Fifth, the mix can be added to non-cholesterol-containing and fat-free foods and beverages. Sixth, the mix is prepared in a manner to prevent self-association of sitostanol as occurs when it is dried from organic solvents containing sitostanol and solubilizing agents. Seventh, the mix may contain lysolecithin. The mix herein referenced has the advantage of a high degree of bioavailability as assayed with artificial bile in vitro. This is significant and something that cannot be achieved with fat carrier systems.

The composition is useful for reducing cholesterol absorption in humans at doses between 10 and 1000 mg, and a preferred dose is 100–300 mg. The dose is less than required by current protocols. The composition may be used in capsule or tablet form as a drug or dietary supplement. Alternatively, it may be used in foods as a food additive or substance generally recognized as safe for human consumption.

In preparation of the composition useful for reducing cholesterol in highly bioavailable form, the first step is to provide an aqueous homogeneous micellar mix of the plant sterol with a phospholipid.

The preferred method is to use sitostanol because only small amounts are absorbed in the small intestine, but on the other hand, this plant sterol shows high inhibition of cholesterol absorption. Similar compounds are also suitable, including sitosterol, campesterol, campestanol, stigmasterol. Moreover, lignans, such as sesamin, and saponins are also useful for this purpose, but sitostanol is preferred.

The preferred phospholipid is lecithin. However, as explained below, the most preferred phospholipid system useful to enhance the bioavailability is a mix of lecithin and lysolecithin. Where the mix is used, it is preferred that the mole ratio of lecithin to lysolecithin be at least 1:0.2, preferably 1:0.5.

In this first step, the aqueous homogeneous mixture of the plant sterol and the phospholipid are homogeneously mixed to provide a micellar mix. The preferred mixing form is a high shear mixing. By way of example, vortexing, sonicating, passing through a small orifice such as a French press or other mixing means may be employed. The most preferred mixing is sonication. This disperses the material and enhances the formation of a micellar mix that contains vesicles, the majority of which contain some plant sterol and some lecithin.

Generally, with respect to sonication, any method that is commonly used for preparation of emulsions can be used to prepare homogeneous mixtures of the plant sterol and the lecithin or lysolecithin, either alone or in combination. For example, Waring blenders, or other high shear mixers can provide acceptable results. Microfluidizers can be used. In this latter procedure, the plant sterol and the emulsifier or lecithin are forced through ceramic capillaries under high pressure. Where the preferred sonication technique is used, a time within the range of 1.5 minutes to about 4 minutes for sonication is sufficient. On small scale experiments, sonication is typically performed in about 1.5 minutes.

The drying process is not critical, so long as it does not destroy the vesicular complex formed between the plant sterol and the phospholipid. Generally, nondrastic drying procedures are preferred such as vacuum drying, freeze drying or low-temperature ambient air drying. Where heat is employed, the temperature at atmospheric conditions should not exceed 0° C.

As earlier explained, the dosage of the dry powder may be within the range of 10 to 1000 mg per day, and a preferred dose being 25 to 300 mg per day. The most preferred doses to achieve significant cholesterol absorption reduction levels are achieved at a dose range of from 100 mg to 300 mg two to three times daily.

The following examples are offered to further illustrate, but not limit the process of the present invention.

In these examples sitostanol is used as an example of a phytosterol and lecithin of a phospholipid. However, other phytosterols and phospholipids might be used, provided that the phospholipids increase the solubility of the phytosterols in bile salt micelles and the phytosterols reduce cholesterol absorption.

Phytosterols, as used here, mean sterols such as sitostanol, sitosterol, campesterol, stigmasterol, saponins, lignans, aromatic and isoprenoid natural products, and their derivatives and reduction products. Phospholipids, as used here, mean glycerophospholipids and sphingolipids, as well as their derivatives, such as lysophospholipids.

EXAMPLE 1

Sitostanol, tracer amount of [$^3$H] sitostanol, and other compounds that are found in the gut or that are commonly used as food additives were mixed together in chloroform solution at a fixed mole ratio. An aliquot, containing 1.2 $\mu$Mol of sitostanol, was transferred to an evacuation tube and the solvent was removed under reduced pressure (<50 mtorr). The experiment was initiated by adding 0.5 mL of artificial bile (8 mM sodium taurocholate containing 5 mM soy lecithin and 0.15 mM NaCl, pH 7.4) followed by rotation at 8 rev/min for 30 min at 37° C. The tube was then centrifuged for 1 minute at 17,000 xg to precipitate any solid material, the supernatant was removed and added to scintillation fluid for measurement of radioactivity, and the percent of radioactivity in the artificial bile supernatant was calculated. Table I below summarizes the solubility of sitostanol mixtures in the presence of artificial bile salt.

TABLE 1

| Composition of Sterol Mixture Dried from chloroform | Soluble Sterol, % |
|---|---|
| Sitostanol Alone | 2.3 |
| Sitostanol + Tween-20 1:1 by weight | 7.8 |
| Sitostanol + Taurocholate 1:1 by weight | 57.7 |
| Sitostanol + Monoolein + Diolein 1:1:1 by weight | 14.5 |
| Sitostanol + Lecithin 1:1 by weight | 38.2 |
| Sitostanol + Lysolecithin 1:1 by weight | 8.0 |
| Sitostanol + Lecithin + Lysolecithin 1:1:0.5 by weight | 97.9 |

As shown in line 1 of Table 1, sitostanol alone is poorly soluble in artificial bile salt (2.3%), and the addition of Tween-20, a polysorbate emulsifier used in foods, increases the solubility slightly to 7.8% (line 2). Sitostanol solubility can be enhanced 25-fold, from 2.3% to 57.7%, if it is dried in the presence of an ionic detergent, such as the bile salt sodium taurocholate (line 3). Since bile salt is a component of the digestive process, other compounds that are found in the gastrointestinal system were also tested. Monoolein and diolein are the products of dietary fat digestion, but as shown in line 4, they only produced a modest enhancement of solubility, 2.3% to 14.5%. Bile contains lecithin, and this phospholipid increased sitostanol solubility from 2.3% to 38.2% (line 5). However, the reaction product of phospholipase $A_2$ hydrolysis of lecithin, lysolecithin, produced a slight increase in sitostanol solubility, 2.3% to 8.0% (line 6). Surprisingly, when lecithin and lysolecithin were mixed together with sitostanol, the resulting solid mixture produced almost complete solubility of the sterol, 97.9% (line 7). Taken together, these data indicate that solid sitostanol does not readily dissolve in artificial bile, but that it can be made soluble to a varying degree by including other compounds in solid mixture. Moreover, a compound (lysolecithin) that by itself has little effect on sitostanol solubility can have a marked outcome when it is used in combination with other agents (lecithin).

EXAMPLE 2

Sitostanol, tracer amount of [$^3$H]sitostanol and lecithin, were mixed together in chloroform. Two aliquots containing 1.2 $\mu$Mol of sitostanol were removed and the chloroform solvent was removed under vacuum as described in Example 1. One aliquot was used without further preparation and to the other 500 $\mu$l water was added and the sample mixture was sonicated for 5 minutes on 40% power with a Fisher Sonic Dismembrator Model 300 equipped with a microtip. The sample was then frozen with dry ice acetone and lyophilized to remove water. It is essential to maintain the temperature of the sample below freezing in order to prevent precipitation of sitostanol from the mixture. The solubility of each of these samples in artificial bile was then determined as described in Example 1, and the results are shown in the Table below.

TABLE 2

| Sample Drying Method | Soluble Sterol, % |
|---|---|
| Sitostanol dried from chloroform | 2.3 |
| Sitostanol/Lecithin (1:1 mole ratio) dried from chloroform | 38.2 |
| Sitostanol/Lecithin (1:1 mole ratio) sonicated in water, lyophilized | 89.7 |

The data show the importance of lecithin in solubilizing sitostanol. However, the method of drying the sitostanol/lecithin mixture also affects the subsequent dissolution of the sterol. When the mixture is dried from chloroform, 38.2% of the sterol is solubilized by artificial bile. In contrast, when the mixture is sonicated and then lyophilized, solubilization increases to 89.7%. This shows that dispersing sitostanol/lecithin in aqueous medium followed by removal of water is a preferred method for preparing sitostanol/lecithin mixtures.

EXAMPLE 3

The effectiveness of variable amounts of lecithin to solubilize sitostanol was studied as in Example #1, except that after rotation at 37° for 30 min residual sedimenting sitostanol was re-extracted twice by vortexing with 0.5 ml additional artificial bile and recentrifuging. The following results were obtained:

TABLE 3

| Sitostanol:Lecithin Mole Ratio | Soluble Sterol,% |
|---|---|
| 1:1 | 53.1 |
| 1:2 | 67.9 |
| 1:10 | 67.6 |

These data show that even with repeated extraction and addition of a tenfold excess of lecithin, a significant amount of sitostanol (32%) remained insoluble. When [$^3$H] phosphatidylcholine was added as a tracer instead of [$^3$H] sitostanol, the amount of lecithin solubilized was 93.3%. This indicates that lecithin was nearly quantitatively extracted from the dried sitostanol/lecithin complex, whereas a limiting amount of sitostanol remained. Thus, methods to solubilize sitostanol in artificial bile must take into consideration the existence of residual insoluble sitostanol. Drying sitostanol/lecithin mixtures from a more polar solvent such as ethanol or a less polar solvent such as hexane gave similar results.

EXAMPLE 4

The effect of sonicated sitostanol/lecithin vesicles on human cholesterol absorption was compared to that of solid sitostanol dosed in the presence of sonicated lecithin. Sitostanol was dehydrated by twice dissolving in chloroform and evaporating, and was then ground to a powder in a mortar and pestle. To prepare the sitostanol/lecithin vesicles in a 1:3 mole ratio, 2.00 gm of sterol was added to 11.3 gm of purified soy lecithin in a 150 mL glass beaker. Chloroform was added with stirring to solubilize both components, and the solvent was then removed by incubating in a sand bath at 65° C. Soy lecithin (11.3 g) without sitostanol was prepared in the same manner. When all the solvent was removed, the beakers were placed in a lyophilization jar, and the residual chloroform was removed under vacuum for at least 24 hr. The solid in each beaker was then broken up with a spatula, 120 mL of deionized water was added, and the suspension was stirred vigorously for one hour. Vesicles were prepared by sonicating the contents of each beaker with a Branson Sonifier (setting 7) equipped with a small tip. During sonication, the beaker was immersed in a room temperature water bath. Vesicles containing lecithin alone were formed in 15–30 min, but those containing both sterol and lecithin required 30–45 min. The samples were then centrifuged at 10,000 xg for 10 min and passed through a 5 $\mu$ filter. The mean diameter of the vesicles determined on a Zetasizer that had been calibrated with a 250 nm standard was 204.7 nm for lecithin vesicles and 247.2 nm for the sitostanol/lecithin vesicles. The concentration of sitostanol was measured enzymatically. After preparation and characterization, the vesicles were stored overnight in a refrigerator at 4° C. The next day samples were diluted to 60 ml with water and 500 mg lemon flavored Crystal Light (Kraft Foods, Inc.) was added. Three U.S.P. stomach capsules were filled with a total of 1 g sitostanol powder or 1 g glucose placebo for each subject.

Six normal subjects underwent three cholesterol absorption tests in random order separated by 2 weeks. For each test a National Cholesterol Education Program Step 1 diet was consumed for 8 days beginning on day 1 of the study. On day 4, a standardized test breakfast was consumed consisting of 240 mL orange juice, 240 mL whole milk, 21 gm corn flakes and a 60 gm bagel saturated with 40 mg [26,26,26,27,27,27—$^2$H$_6$] cholesterol tracer dissolved in 2.5 mL corn oil. Each subject also consumed a drink containing either sitostanol/lecithin vesicles or lecithin vesicles and three capsules containing either sitostanol powder or glucose placebo. The concentration of deuterated cholesterol tracer in plasma cholesterol on days 7 and 8 was measured by negative ion methane chemical ionization gas chromatography/mass spectrometry. Reduction in cholesterol absorption was determined by dividing the mean deuterated cholesterol concentration on days 7 and 8 by that observed during the test that contained only lecithin vesicles and glucose capsules and expressing it as a percent. The following results were obtained:

TABLE 4

| Treatment Given | Reduction in Cholesterol Absorption |
|---|---|
| 1000 mg sitostanol powder | 11.3 ± 7.4% (p = 0.2) |
| 700 mg sitostanol/lecithin vesicles | 36.7 ± 4.2% (p = 0.003) |

These results show that, compared to placebo, 1000 mg sitostanol powder did not reduce cholesterol absorption significantly. This is consistent with previous reports showing that only multi-gram sitostanol doses reduce cholesterol absorption. However, 700 mg sitostanol/lecithin vesicles reduced cholesterol absorption by 37%, showing that properly formulated sitostanol is active and bioavailable.

EXAMPLE 5

To demonstrate that sitostanol/lecithin reduces cholesterol absorption in a pharmacological dose-response fashion, it was given in reduced amount to 5 of the 6 subjects of Example 4 during four additional cholesterol absorption tests. A dose of 300 mg sitostanol in sitostanol/lecithin vesicles was compared to lecithin placebo, and a dose of 150 mg sitostanol in sitostanol/lecithin vesicles was compared to another lecithin placebo. No capsules of solid sitostanol or placebo were given. The following results were obtained:

TABLE 5

| Treatment Given | Reduction in Cholesterol Absorption |
|---|---|
| 300 mg Sitostanol/Lecithin Vesicles | 34.4 ± 5.8% (p = 0.01) |
| 95 mg sitostanol/Lecithin Vesicles | 5.6 ± 7.2% (not significant) |

Cholesterol absorption was reduced nearly as much by the 300 mg dose as the 700 mg dose, indicating that this dose is saturating. This is consistent with previous work showing that phytosterols do not completely block cholesterol absorption. There is no significant effect on cholesterol absorption at a dose of 95 mg.

It can be seen from the above examples that the composition prepared in accordance with the process of this invention is bioavailable in vitro in bile, will significantly reduce cholesterol absorption, and that in general all of the objectives of the invention are achieved.

It should be understood that certain modifications should be and will be apparent to those of ordinary skill in the art, and that such modifications to the precise procedures in compositions set forth herein are intended to come within the spirit and scope of the invention either literally or by doctrine of equivalents. In this light, the following claims are asserted.

What is claimed is:

1. A composition in solid, but water soluble form for reducing cholesterol absorption, comprising:

an aqueous homogeneous micellar mix of a plant sterol and lecithin which has been dried to a finely divided water soluble powder;

the mole ratio of said plant sterol to lecithin being within the range of 1:1 to 1:10.

2. The composition of claim 1 wherein the mole ratio of plant sterol to lecithin is at least 1:2.

3. The composition of claim 1 wherein the mole ratio of plant sterol to lecithin is within the range of 1:2 to 1:4.

4. The composition of claim 1 wherein the micellar mix is a mix of vesicles, the majority of which contain some plant sterol and some lecithin.

5. The composition of claim 1 wherein the plant sterol is sitostanol.

6. The composition of claim 1 further comprising a food.

7. A method for reducing cholesterol absorption from food products, comprising the steps of:

adding finely divided water soluble powder formed from an aqueous homogeneous micellar mix of a plant sterol and lecithin which has been dried to a food product;

the mole ratio of said plant sterol to said lecithin of said powder being within the range of 1:1 to 1:10;

the amount added to said food product being sufficient to provide a dose of from about 100 mg to about 1000 mg of sitostanol.

8. The method of claim 7 wherein the dose is from 100 mg to 300 mg, provided at least 2 to 3 times daily.

9. A food composition comprising:

a food containing cholesterol and a food additive wherein the food additive is a finely divided water soluble solid form homogeneous micellar mix of sitostanol and lecithin with a mole ratio of sitostanol to lecithin being within the range of 1:1 to 1:10 in the added mix.

10. The composition of claim 9 wherein the food product is solid food product.

11. The composition of claim 9 wherein the food product is a beverage.

12. A composition for reducing cholesterol absorption comprising:

an aqueous homogeneous micellar mix of a plant sterol and lecithin and lysolecithin mix which has been dried to a finely divided water soluble powder;

the mole ratio of said plant sterol to said lecithin and lysolecithin mix being within the range of 1:1 to 1:10, and in said mix said lysolecithin having a mole ratio to the lecithin of at least 0.2.

* * * * *